(12) United States Patent
Blanchard

(10) Patent No.: US 8,257,757 B1
(45) Date of Patent: Sep. 4, 2012

(54) RODENT CONTROL COMPOSITION

(76) Inventor: James Blanchard, Granby, CT (US)

( * ) Notice: Subject to any disclaimer, the term of this patent is extended or adjusted under 35 U.S.C. 154(b) by 65 days.

(21) Appl. No.: 12/797,354

(22) Filed: Jun. 9, 2010

(51) Int. Cl.
*A61K 36/48* (2006.01)
*A61K 36/899* (2006.01)

(52) U.S. Cl. .......................... 424/757; 424/750

(58) Field of Classification Search .................. None
See application file for complete search history.

(56) References Cited

U.S. PATENT DOCUMENTS

| | | | |
|---|---|---|---|
| 3,624,198 A | 11/1971 | Arbaugh |
| 4,933,371 A | 6/1990 | Hink |
| 5,356,881 A | 10/1994 | Verbiscar |
| 5,720,951 A | 2/1998 | Baker |
| 6,689,796 B1 | 2/2004 | Johnson |
| 2006/0277818 A1 | 12/2006 | Scherman |

OTHER PUBLICATIONS

Ratkill.com. Retrieved from the internet. <http://web.archive.org/web/20010807023646/http://ratkill.com/enemy.html>. Retrieved on Sep. 30, 2011. Web archive date Jul. 8, 2001. 5 pages.*
Uneke. Integrated pest management for developing countries: a systemic overview. Nova Publishers. 2007. p. 33.*
Vick. Vick's Monthly Magazine. vol. 4. 1881. p. 108.*
United States Department of Agriculture. Year of agriculture. 1908. U.S. G.P.O. 1909. p. 427.*
Kinghorn. Toxic plants. Columbia University Press. 19179. p. 127.*
Sandberg et al. Natural remedies:their origins and uses. CRC Press. 2001. p. 144.*
Thinkexist.com. Retrieved from the internet. Retrieved on Oct. 4, 2011. <http://thinkexist.com/dictionary/meaning/easter_lily/>.1 page.*
Wikipedia.org. Retrieved from the internet. Retrieved on Oct. 3, 2011. <http://en.wikipedia.org/wiki/Easter_lily>. 1 page.*
Rozanski et al. A color handbook of small animal emergency and critical care medicine. Manson Publishing. 2007. pp. 95-96.*
Langalais. Lilies an cause death in cats. Times. Cambridge. Mar. 24, 2005. p. 25 (1 page in Proquest).*

* cited by examiner

*Primary Examiner* — Melenie McCormick
(74) *Attorney, Agent, or Firm* — Neustel Law Offices

(57) ABSTRACT

An environmentally safe rodent control composition for exterminating rodents such as mice and rats without the use of chemicals. The rodent control composition generally includes an attractant base, a digestive upset catalyst such as oleander leaves, a coma catalyst such as lily flowers, a paralysis catalyst such as water hemlock roots and a cardiac arrest catalyst such as lily of valley berries. The attractant base is generally comprised of materials which attract a rodent to the present invention and encourage a rodent to ingest the same. The attractant base may be comprised of such materials as peanut butter, mixed bird seed, mixed grains and the like. A rodent will generally die within 12-36 hours after ingestion of the present composition, which does not include any chemicals or additives which are damaging to the environment.

1 Claim, No Drawings

RODENT CONTROL COMPOSITION

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to a composition for controlling rodents and more specifically it relates to an environmentally safe rodent control composition for exterminating rodents such as mice and rats without the use of chemicals.

2. Description of the Related Art

Any discussion of the related art throughout the specification should in no way be considered as an admission that such related art is widely known or forms part of common general knowledge in the field.

Mice, rats and other rodents have plagued humankind since the beginning of civilization. In the middle ages, large populations within Europe were infected by and subsequently died of a plague transmitted by such rodents. As such, humans have sought numerous ways for exterminating or controlling rodent populations to prevent health and sanitation problems from arising and/or spreading.

In the past, rodents have been controlled through use of mechanical devices or chemical compositions. Such mechanical devices have included devices such as mousetraps which utilize bait such as cheese and a mechanical apparatus for exterminating the rodent in question, such as a metallic bar or other apparatuses which acts to break the neck of a rodent. The presence of these mechanical devices can often be forgotten, which can lead to injury from a person indavertantly stepping onto the device. Further, such mechanical devices often lead to injury in setting the trap or placing the bait. Finally, the vision of a rodent with a broken neck can be disturbing to some individuals. With respect to chemical compositions, such compositions are often toxic (presenting risk to children who may unwittingly consume the compositions) or damaging to the environment. Because of the inherent problems with the related art, there is a need for a new and improved environmentally safe rodent control composition for exterminating rodents such as mice and rats without the use of chemicals.

BRIEF SUMMARY OF THE INVENTION

An environmentally safe rodent control composition for exterminating rodents such as mice and rats without the use of chemicals. The invention generally relates to a rodent control composition which includes an attractant base, a digestive upset catalyst such as oleander leaves, a coma catalyst such as lily flowers, a paralysis catalyst such as water hemlock roots and a cardiac arrest catalyst such as lily of valley berries. The attractant base is generally comprised of materials which attract a rodent to the present invention and encourage a rodent to ingest the same. The attractant base may be comprised of such materials as peanut butter, mixed bird seed, mixed grains and the like. A rodent will generally die within 12-36 hours after ingestion of the present composition.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

DETAILED DESCRIPTION OF THE INVENTION

A. Overview.

The present invention is directed to an environmentally safe rodent control composition for exterminating rodents such as mice and rats without the use of chemicals. The composition of the present invention is generally comprised of an attractant base, a digestive upset catalyst such as oleander leaves, a coma catalyst such as lily flowers, a paralysis catalyst such as water hemlock roots and a cardiac arrest catalyst such as lily of valley berries. The attractant base is generally comprised of materials which attract a rodent to the present invention and encourage a rodent to ingest the same. The attractant base may be comprised of such materials as peanut butter, mixed bird seed, mixed grains and the like. A rodent will generally die within 12-36 hours after ingestion of the present composition.

B. Attractant Base.

The rodent control composition of the present invention will generally include an attractant base for enticing a rodent to consume the composition. The attractant base of the present invention will generally be comprised of materials with traits desirable for a rodent. Specifically, the attractant base will preferably be comprised of a material or composition of materials which has a smell, taste and appearance which will encourage a rodent encountering the present invention to ingest the same.

The attractant base of the present invention may be comprised of a wide range of materials. Preferably, the attractant base will not include any chemicals or chemical composition. The attractant base may include such materials as bird seed, mixed grains, ground milk chocolate and/or combinations thereof. It is also appreciated that other materials such as cheese or other dairy products may be utilized in the attractant base.

In a first embodiment of the present invention, the attractant base will preferably be comprised of sixteen ounces of peanut butter, three ounces of mixed bird seed, two ounces of mixed grains and one ounce of ground milk chocolate. Such an attractant base has been shown to entice rodents to consume the composition.

It should be appreciated by one of ordinary skill in the art that the attractant base of the present invention may be comprised of various other compositions of materials. The volumes of each ingredient disclosed above is merely a preferred embodiment, and should not be construed as in any way limiting the scope of the present invention. Various other types of materials and volumes of each material may be utilized without affecting the overall operation of the present invention, so long as the attractant base is successful in luring a rodent to the composition and enticing the rodent to consume the composition.

C. Oleander Leaves.

The present invention will generally include a catalyst for causing digestive upset in the consuming rodent. Generally, the digestive upset catalyst utilized with the present invention will be comprised of oleander.

Oleander is an evergreen shrub or small tree which includes clusters of flowers at the end of each branch. Oleander is known as one of the world's most poisonous plants and includes a number of toxic compounds, including oleandrin and neriine. These toxic compounds are generally found in all parts of the oleander plant and particularly concentrated in its sap.

Ingestion of oleander can lead to both gastrointestinal and cardiac effects. Gastrointestinal effects generally include nausea and vomiting, excessive salivation, abdominal pain and/or diarrhea. Cardiac effects may include irregular or erratic heart rhythm. As such, the use of oleander in the present invention will generally lead to digestive upset in the consuming rodent and may induce cardiac irregularities which can further accelerate the death of the consuming rodent.

While various parts of the oleander plant may be utilized with the present invention, it is preferable that large leaves of the oleander plant be ground up and included in the composition for inducing digestive upset in a consuming rodent. Further, while various amounts of oleander may be utilized in different embodiments of the present invention, it is preferable that approximately eight to ten large oleander leaves be utilized in the composition of the present invention to ensure the proper effects on a consuming rodent. However, the scope of the present invention should in no way be limited to a specific part of the oleander plant or a specific volume of oleander-based materials.

D. Lily Flowers.

The present invention will also generally include a catalyst for causing convulsions and coma in a consuming rodent. Generally, the coma catalyst utilized with the present invention will be comprised of ground lily flowers.

Lilies are generally comprised of any plant of the Lilium genus. Lilies are generally flowering plants which are grown from bulbs. There are approximately 110 species in the lily family. Ingestion of parts from lilies has been shown to be extremely toxic and encourage the onset of renal failure, convulsions and/or coma in ingesting small animals.

Examples of types of lilies which may be utilized with the present invention include Easter Lily, Tiger Lily, Day Lily, Asian Lily and the like. It should be appreciated by one of ordinary skill of the art that any type of lily may be utilized with the present invention so long as the lily includes the requisite toxicity for causing renal failure, convulsions and/or coma in an ingesting rodent.

While various parts of the lily plant may be utilized with the composition of the present invention, it is preferable to utilize the flowers of the lily plant within the composition. Further, it should be appreciated that various parts other than the flower of the lily plant may be utilized so long as the requisite negative health effects are provided. As such, the scope of the present invention should not be construed as being limited solely to the flowers of the lily plant.

While various amounts of lily flowers may be utilized, a preferred embodiment of the present invention utilizes eight to ten large lily flowers, which are ground and mixed with the other components of the composition. However, it should be appreciated by one of ordinary skill in the art that more or less lily flowers may be utilized with the present invention without affecting its overall operation, so long as the requisite level of toxicity is present to impart negative health effects (such as renal failure, convulsions and/or coma) in the ingesting rodent.

E. Water Hemlock Roots.

The present invention will also generally include a catalyst for the progressive paralysis of the central nervous system within an ingesting rodent. Such a catalyst will preferably be comprised of ground water hemlock roots.

Water hemlock is generally comprised of any of the four species of highly poisonous plants in the family Apiaceae. Water hemlock has been shown to contain high levels of cicutoxin in all parts of the plant during any stage of its development. When consumed, cicutoxin generally acts as a stimulant in the central nervous system of the consuming rodent, causing seizures and progressive paralysis of the central nervous system. Other potential side effects of the consumption of water hemlock may include nausea, vomiting, abdominal pain, tremors, confusion, weakness, dizziness and drowsiness. The ingestion of water hemlock can additionally lead to death due to respiratory failure or ventricular fibrillation.

While any part of the water hemlock plant may be utilized for its toxic effects, it is preferable to utilize the roots of water hemlock plants in the present invention. Preferably, the roots of a water hemlock plant will be ground up and mixed with the other components of the composition of the present invention. However, it is appreciated by one of ordinary skill in the art that various other portions and parts of the water hemlock plant may be utilized in the present invention so long as the toxic effects of the cicutoxin within the plant are imparted to the composition as a whole.

While various amounts of water hemlock roots may be utilized with the present invention, a preferred embodiment utilizes two to three large water hemlock roots. The water hemlock roots will preferably be fresh so as to impart the maximum amount of toxicity to the composition as a whole, though it is appreciated that older water hemlock roots may be utilized in the absence of fresh water hemlock roots. It should also be appreciated by one of ordinary skill in the art that more or less water hemlock roots may be utilized with the present invention without affecting its overall operation, so long as the requisite level of toxicity is present to impart negative health effects (such as central nervous system paralysis) in the ingesting rodent.

F. Lily of the Valley Berries.

The present invention will also generally include a catalyst for inducing cardiac arrest within an ingesting rodent. Such a catalyst will preferably be comprised of ground berries from a lily of the valley plant.

The lily of the valley plant is a perennial plant which is highly poisonous. The lily of the valley plant generally produces small berries. Lily of the valley plants have been shown to include approximately 37 different cardiac glycosides, including convallarin, convallamarin and convallatoxin. Lily of the valley plants have been shown to induce cardiac arrest in ingesting rodents.

While any part of the lily of the valley plant may be utilized for its toxic effects, it is preferable to utilize the berries of lily of the valley plant in the present invention. Preferably, the berries of a lily of the valley plant will be ground up and mixed with the other components of the composition of the present invention. However, it is appreciated by one of ordinary skill in the art that various other portions and parts of the lily of the valley plant may be utilized in the present invention so long as the toxic effects of the cadiac glycosides within the plant are imparted to the composition as a whole.

While various amounts of berries of a lily of the valley plant may be utilized with the present invention, a preferred embodiment utilizes three to six berries. It should be appreciated by one of ordinary skill in the art that more or less berries of a lily of the valley plant may be utilized with the present invention without affecting its overall operation, so long as the requisite level of toxicity is present to impart negative health effects (such as cardiac arrest) in the ingesting rodent.

G. Preparation of Preferred Embodiment of the Composition.

To prepare the rodent control composition of the present invention, the ingredients need only be ground up and mixed together. One preferred embodiment of the present invention is comprised of sixteen ounces of peanut butter, three ounces of mixed bird seed, two ounces of mixed grains, one ounce of ground hard milk chocolate, ten ground large oleander leaves, ten large ground lily flowers, three large ground fresh water hemlock roots and six ground lily of the valley berries.

A second embodiment of the present invention is comprised of sixteen ounces of peanut butter, three ounces of mixed bird seed, two ounces of mixed grains, one ounce of ground hard milk chocolate, eight ground large oleander leaves, two ground fresh water hemlock roots, eight ground lily flowers and three ground lily of the valley berries.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A rodent control composition consisting of:
   2 ground roots of a water hemlock plant for inducing progressive paralysis of the central nervous system in said rodent;
   8-10 ground flowers of a tiger lily plant;
   8 ground leaves of an oleander plant;
   3 ground berries of a lily of the valley plant; and
   an attractant base for attracting a rodent, wherein the attractant base consists of 73% peanut butter, 13% bird seed, 5% chocolate and 9% mixed grains.

* * * * *